United States Patent
Katerkamp et al.

(12) 
(10) Patent No.: US 6,730,471 B1
(45) Date of Patent: May 4, 2004

(54) METHOD, VESSEL AND DEVICE FOR MONITORING METABOLIC ACTIVITY OF CELL CULTURES IN LIQUID MEDIA

(75) Inventors: Andreas Katerkamp, Munster (DE); Göran Key, Osnabruck (DE); Gabriele Chemnitius, Munster (DE)

(73) Assignee: Institut fur Chemo-und Biosensorik Munster e.V., Munster (DE)

( * ) Notice: Subject to any disclaimer, the term of this patent is extended or adjusted under 35 U.S.C. 154(b) by 0 days.

(21) Appl. No.: 09/890,228

(22) PCT Filed: Jan. 5, 2000

(86) PCT No.: PCT/DE00/00071
§ 371 (c)(1),
(2), (4) Date: Jul. 27, 2001

(87) PCT Pub. No.: WO00/44876
PCT Pub. Date: Aug. 3, 2000

(30) Foreign Application Priority Data

Jan. 29, 1999 (DE) .......................... 199 03 506

(51) Int. Cl.[7] .......................... C12Q 1/02; C12M 3/00
(52) U.S. Cl. .................. 435/4; 435/287.1; 435/287.5; 435/288.7
(58) Field of Search .................. 435/4, 287.1, 287.5, 435/280.1

(56) References Cited

U.S. PATENT DOCUMENTS 4,548,907 A 10/1985 Seitz et al.
5,601,997 A 2/1997 Tchao

FOREIGN PATENT DOCUMENTS

| EP | 344313 A1 * | 12/1989 | ............. C08F/8/42 |
|----|----|----|----|
| EP | 0 810 281 A2 | 12/1997 | |
| WO | WO 87/00023 A1 | 1/1987 | |
| WO | WO 88/06287 A1 | 8/1988 | |
| WO | WO 95/03254 A1 | 2/1995 | |
| WO | WO 99/47922 A2 | 9/1999 | |

OTHER PUBLICATIONS

Randers–Eichhorn et al., "Noninvasive Oxygen Measurements and Mass Transfer Considerations in Tissue Culture Flasks" (Aug. 20, 1996) Biotechnol. Bioengineer., 51(4), 466–478.*

* cited by examiner

*Primary Examiner*—Jon P. Weber
(74) *Attorney, Agent, or Firm*—Leydig Voit & Mayer, Ltd.

(57) ABSTRACT

The invention relates to a method for monitoring metabolic activity of cells in liquid media, to an appropriate vessel and to a device for implementing said method. The invention aimes at enhancing measuring accuracy and reducing the costs involved in monitoring oxygen consumption and thus metabolic activity in culture cells. To this end, oxygen concentration is optically determined with the aid of sensor membranes in a liquid medium located in partially oxygen permeable vessels. Then, the measured oxygen concentrations in the vessels containing culture cells in a liquid medium are compared with the measured oxygen concentration in a vessel containing only such a liquid medium without cells and/or with an oxygen concentration calculated using the measured values of other parameters.

22 Claims, 12 Drawing Sheets

METHOD, VESSEL AND DEVICE FOR MONITORING METABOLIC ACTIVITY OF CELL CULTURES IN LIQUID MEDIA

The invention relates to a method for monitoring metabolic activity of cells in liquid media, to a vessel particularly appropriate for this, and to a respective device for implementing said method.

In the vessels cells to be cultivated as well as a liquid medium are contained wherein the latter concerns with a conventional nutritive solution corresponding to the used cells, if necessary. The solution according to the invention can be employed for the most different cells and the most different studies, in particular in the pharmacological field wherein the metabolic activity of the cells can be monitored over a longer period. For example, monitoring the action with cytotoxic and biocompatibility tests, and optimizing the culture conditions for the production of biological molecules can be carried out.

Commonly, the major nutrient source for cell cultures is glucose which can be converted into lactate by means of aerobic glycolysis or oxidatively with the oxygen consumption and formation of carbon dioxide. Then, many influences of the physiology of a cell have an affect on its metabolic activity such that oxygen consumption is accordingly allowed to vary as well. Starting from the connection between the metabolic activity of cells with respect to the oxygen consumption, and e.g. the glucose consumption and L-glutamine consumption or the generation of lactate it is allowed to conclude the condition of the monitored cells, and as a result the influence of the respective culture conditions.

Based upon these findings, int. al., in "Noninvasive Oxygen Measurements and Mass Transfer Considerations in Tissue Culture Flasks" published in Biotechnology and Bioengineering, Vol. 51, pp. 466 to 478, it has been described by Lisa Randers-Eichhorn, how the oxygen consumption of cells cultivated in T-flasks can be determined by means of an optical measurement. Therein, it is suggested to arrange sensor membranes containing fluorescent indicators immediately on the flask bottom, and in the gas space above the nutritive solution within such a T-flask. During the measurement of oxygen concentration with such sensor membranes, the well known physical phenomenon of fluorescent erasure of known fluorescent dyes such as e.g. complexes of Ruthenium (II) is employed due to the influence of oxygen wherein the respective fluorescent intensity changes with the continuous excitation according to the oxygen concentration and the partial pressure of oxygen, respectively. For the determination of oxygen concentration the respective fluorescent intensity immediately, but also the fluorescence life can be measured, and the oxygen concentration can be determined according to a known calibration.

The set-up of measuring instruments described in this document, in particular the arrangement of the sensor membrane on the bottom of the T-flasks, and the neglected determination of some important influence quantities is not suitable to conclude the metabolic activity of the culture cells from oxygen consumption.

The charge of oxygen into the nutritive solution occurs for the most part through the interface of the nutritive solution toward the gas space, therefore here toward the gas space in the T-flask, and the consumption occurs by the cells being present on the bottom of the T-flask. The maximum enabled oxygen concentration which can be achieved within the nutritive solution is the saturation concentration of oxygen $C_{Sat}$ (of mg/l) which, according to the equation, $$C_{sat}=([p-\gamma^*p_w(T)]/p_0^*\alpha(T)^*X_{O2}$$

is a function of the total gas pressure p (mbar), the relative humidity of air $\gamma$ (in values from 0 to 1, wherein 1 corresponds to a value of 100%, and 0 corresponds to a value of 0%), the partial pressure of water vapour $p_w(T)$ (mbar) as a function of the temperature T, the mole fraction of oxygen $X_{O2}$ within the gas space of the T-flasks, the Bunsen absorption coefficient $\alpha(T)$ (mg/l) as a function of the temperature T and the normal pressure $p_0$=1013 mbar. Then, it is assumed that the gas space and the nutritive solution have the same temperature, and the gas space has been filled with atmospheric air which chemical composition thereof is sufficiently known. These preconditions are commonly present in breeding chambers in which cells will be cultivated. This saturation concentration of oxygen appears directly below the top surface within the nutritive solution. Therefrom, the oxygen is transported by means of different effects such as diffusion and/or convection toward the cells being present on the bottom. In such a system two quantities are significant. On the one hand, this is the consumption rate $k_v$ at which oxygen is consumed by the cells, and on the other hand, the transport rate $k_T$ at which oxygen is transported toward the cells. The two quantities are responsible together for that an oxygen gradient results from the top surface of the nutritive solution toward the bottom including cells. If the consumption rate is now slightly smaller than or equal to the transport rate, thus an oxygen concentration comprising a value of 0 is measured with the oxygen membrane on the bottom below the cells. In this case, the cells do not suffer from an oxygen supply since still sufficient oxygen is transported toward the cells, but which does not arrive toward the sensor membrane below the cells, and which, accordingly, cannot be measured any longer. If the consumption rate further increases, e.g. by spreading out the cells, and the consumption rate becomes greater than the transport rate thus this cannot be monitored any longer with the oxygen membrane located on the bottom below the cells. Furthermore, the saturation concentration of oxygen is a very important quantity in addition to the consumption and transport rates as a function of the total gas pressure, the humidity, the temperature and the mole fraction of oxygen and the partial pressure of oxygen, respectively, within the gas space of the T-flask. A change is causing a change of the oxygen gradient, and thus a change of oxygen concentration at any place between the cells and the top surface of the nutritive solution. Since the parameters of total pressure, humidity and temperature have not been determined or checked in the mentioned documentation, it cannot be excluded that measuring results became falsified due to variations of these parameters.

Therefore, it is the object of the invention to predetermine ways wherein monitoring the oxygen consumption and thus the metabolic activity of culture cells can be achieved in a cost effective manner and with an increased accuracy.

According to the invention this object is achieved with the features of claim 1 for a method, and with the features of claim 11 for an appropriate vessel. Advantageous embodiments and improvements of the invention result from the features mentioned in the subordinate claims.

The solution according to the invention is now assuming from that said cells will be cultivated in vessels using a liquid medium wherein as a rule here it concerns with a respective nutritive solution, and that the metabolic activity thereof takes place through the measurement of oxygen concentration at a location within the liquid medium between the cells consuming oxygen and the part being dominant for the oxygen charge into the liquid medium, which is here the top surface of the nutritive solution. Then, the saturation concentration of oxygen in the liquid medium will be determined according to comparison measurements in a vessel of cell cultures without any cells and/or by means of the determination of the parameters of pressure, humidity, temperature and with a chemical composition being well known and constant, of the ambient gas space, which are here the mole fractions of the gas components and the partial pressures thereof, respectively, in the ambient atmosphere. From the comparison between the saturation concentration of oxygen as a set value and the saturation concentration of oxygen at a location of the oxygen gradient within the vessel including the culture cells as an actual value, the oxygen consumption and thus the metabolic activity of the cells are concluded.

For monitoring, vessels can readily be used in contrast to the prior art which comprise an aperture such that the top surface of the liquid medium can be affected by the ambient atmosphere. In certain cases, however, such an aperture is also allowed to be covered and closed, respectively, with a membrane at least being permeable to oxygen such that entering of undesired germs is prevented.

The oxygen concentration will be preferably measured optically with a sensor membrane suitable thereto which optical characteristics thereof change as a function of the respective oxygen concentration. Thus, in a respective vessel at least one suitable sensor membrane should be placed which is located such that it is arranged above the cell cultures cultivated on the vessel bottom, however, below the top surface of the liquid medium.

If the cells cultivated on the vessel bottom are consuming oxygen, the oxygen concentration within the liquid medium will reduce accordingly, and the oxygen concentration actually measured with the sensor membrane will be determined by the oxygen consumption due to the metabolic activity and oxygen quantity which enters into the liquid medium again occurred due to the gradient of oxygen concentration.

Since the conformities to natural laws with respect to the saturation concentration of oxygen in liquid media are relatively properly known, it is possible to calculate the respective saturation concentration of oxygen within a liquid medium under consideration of known parameters which are in particular here the respective temperature, the pressure and the humidity, such that this calculated value of oxygen concentration can be subjected to a value comparison including the actually measured oxygen concentration to evaluate the oxygen consumption and metabolic activity, respectively, of the cell cultures.

However, it is also possible to carry out a reference measurement wherein a second vessel is used in which merely a nutrient medium being completely identical with the used nutritive solutions with respect to the oxygen diffusion characteristics is used. In such a reference vessel a respective sensor membrane is arranged again preferably at the same place whereby the unaffected oxygen concentration can be measured. The reference oxygen concentration thus measured is also allowed to be subjected to a respective value comparison with the oxygen concentration affected by metabolic activity in order to judge the metabolic activity of the culture cells.

Of course, such a value comparison can also be carried out simultaneously for commonly the calculated oxygen concentration and measurement signal of oxygen concentration in the reference vessel including the oxygen concentration measured under metabolic activities moderated by culture cells.

Moreover, the meaningfulness with the benchmarking of metabolic activity of culture cells can be increased when sensor membranes are placed additionally within the vessels in such a manner here again as the oxygen sensitive membranes which include an oxido-reductase on an oxygen sensitive membrane, and wherein the change of oxygen concentration can be measured by a substrate conversion of the enzyme.

Conveniently, these two different sensor membranes should be arranged at least approximately in the same distance of the cell cultures within the liquid medium. For detecting the concentration of the substrate of oxido-reductase and thus the metabolic activity the fluorescent signals of the oxygen membrane and the second oxygen membrane covered with the supplementary membrane are compared. Then, it can be necessary to substract the signal of the first sensor membrane from the signal of the second sensor membrane so as to achieve the sensor response to the enzymatic test of the oxygen, and thus to determine the substrate concentration. Then, it can also be advantageous to introduce a factor by means of which the different oxygen transport relations in the two oxygen membranes are taken into account. Moreover, for an iteration of the signal of the enzymatic sensor it can also be necessary to use different calibration curves depending on the oxygen concentration within the solution, since oxygen is a co-substrate of the enzymatic reaction. In any case, by means of a determination of the enzymatic activity the metabolic activity of the cells can further be determined independent of oxygen consumption of the culture cells.

Since the metabolic activity of the culture cells changes relatively slowly over longer periods, it is sufficient to measure the respective concentrations in longer periods, for example, in intervals of several minutes in order to monitor the metabolic activity of the respective cell cultures with appropriate accuracy, which results in the effort required for a suitable measurement equipment is allowed to be reduced by means of an enabled multiplex operation.

Since the concentration shall be advantageously measured optically it is necessary to use vessels which are optically transparent in definite areas such that the respective change of optical intensity can be measured with optical waveguides (glass fibers), for example, and an appropriate optical sensor. Then, such an optical waveguide has not to be a direct part of a used vessel, or has not to be connected therewith immediately, but can be located and aligned such that it is merely able to detect the area and parts on one sensor membrane with its aperture. As a result, the measuring location and measuring vessel are readily allowed to be separated locally from each other.

Furthermore, there is a possibility as suggested with the way of multiplex measurement to commonly monitor a plurality of vessels in which the same or different cells are cultivated wherein these each can be taken into account individually one after another by means of a respective circuit of at least one multiplexer, respectively. Hence, a more or less spatial resolution type measurement of concentrations can be carried out. For example, sensor membranes can be used which change their absorption and reflection characteristics, respectively, as a function of the oxygen concentration. Alternatively, establishing from known solutions, it is also possible to employ the phenomenon of fluorescence erasure and to use sensor membranes including known fluorescent dyes which are capable to be fluorescent with the light of particular wavelengths when excited wherein the wavelength of the excitation light and the wavelength of the fluorescent light are different.

In the last mentioned case the concentration can be measured once by means of a direct measurement of the respective fluorescent intensity. However, it is more favourable to determine the fluorescence life since in this case aging and subsequently the well known bleaching behaviour do not affect the measuring accuracy.

The oxygen sensitive sensor membranes can be inserted subsequently as well into the vessels useful for the solution according to the invention by means of different techniques. Such sensor membranes can be selectively deposited locally by dispensing, spraying, dipping or glueing as well. Appropriate placing locations within such vessels are, for example, the interior wall of the vessel in a predetermined distance from the vessel bottom, and landing shaped members projecting beyond the bottom surface of the vessel are particularly appropriate wherein on the upper end face thereof a corresponding sensor membrane can be formed and applied, respectively. In this case, at least the landing shaped members are formed from a material being transparent to the relevant wavelengths such that corresponding monitoring can take place from below through the vessel bottom. The remaining vessel parts then have not to be composed conclusively of another transparent material.

Within a vessel to be used in accordance with the invention two of such landing shaped members can be located spaced apart from each other wherein, on the one hand, an exclusively oxygen sensitive sensor membrane is deposited, and on the other hand, such a supplementary membrane can be deposited which is formed with a membrane coated with an enzymatic oxidase sealed against the liquid medium.

For example, if a greater number of samples is to be simultaneously monitored, it is particularly favourable to form a vessel according to the invention in an analogous manner with the known MicroWell™ Plates wherein in such a MicroWell™ Plate a greater number of receiving spaces (cavities) for the cells to be cultivated are located with the liquid medium in a plurality of rows adjacent to each other. A MicroWell™ Plate formed in this manner can be placed in a breeding chamber then, for example, for the cell cultivation, wherein the excitation light and the fluorescent light can be directed from an appropriate light source via optical waveguides upon the sensor membranes, and the fluorescent light from the sensor membranes toward an appropriate optical sensor. Then, it is possible for both the excitation light and the fluorescent light to be guided through a single optical waveguide. Of course, corresponding light guiding for the two different types of light can be carried out inside two separate optical waveguides. For this, the optical waveguides have merely to be fixed and positioned such that their apertures ensure an optimum fluorescence excitation and an approximately complete detection of the fluorescent light. Then, for fixing and positioning the optical waveguides separate mechanism plates can be used which will be dimensioned and aligned relative to the vessels to be used in accordance with the invention, such that the optical waveguides are located and aligned with respect to the sensor membranes. This configuration is particularly appropriate for vessels formed in a MicroWell™ Plate shaped manner. Favourably, a cavity (well) of such a MicroWell™ Plate shaped member can be used for the reference measurement previously mentioned at the beginning, i.e. merely filled with liquid medium but without cell cultures.

The aspect for MicroWell™ Plate shaped members formed and being useful in accordance with the invention or even other appropriate vessels can be formed according to the common laboratory standards such that they are able to be used as well in the conventional form with the different known laboratory instruments.

The spatial resolution type measurement of different samples cannot only take place with the individual optical waveguides associated with the sensor membranes, however, but there is the possibility as well to use an endoscopy array by means of which the image of a greater number of sensor membranes detected by such an array can be directed upon a CCD camera, for example, such that an isochronous spatial resolution type measurement of different oxygen concentrations is enabled.

In the following the invention will be described in more detail by way of example.

In the drawings

Figure 1:
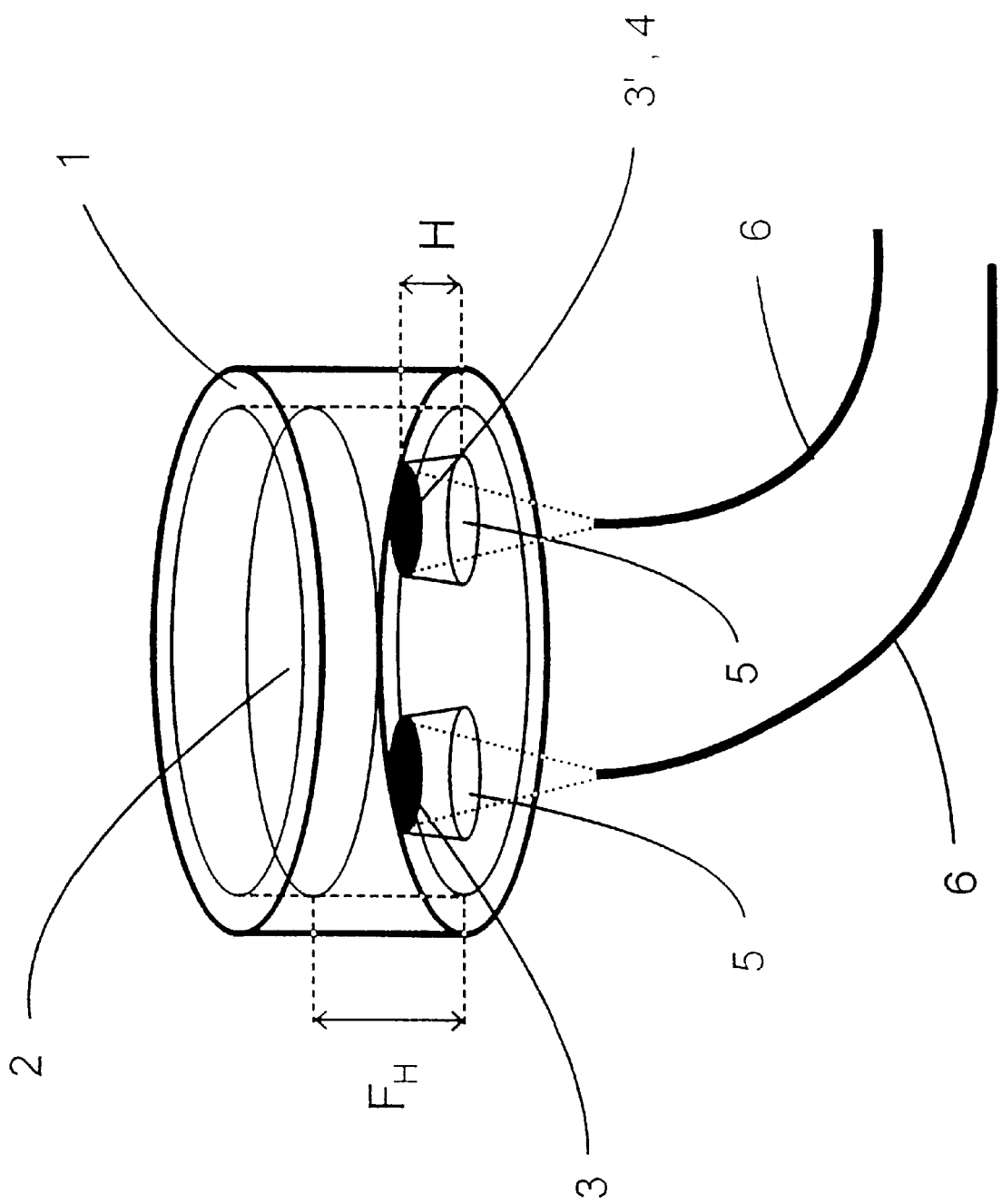
FIG. 1 shows a diagrammatic illustration of an embodiment of a vessel for monitoring metabolic activity of culture cells in liquid media including sensor membranes and optical waveguides.

In FIG. 1 is shown a diagrammatic illustration of an embodiment of vessel 1 for monitoring metabolic activity of cell cultures in liquid media 2.

The vessel 1 illustrated here is predominantly formed cylinder shaped and comprises a transparent bottom plate which is open on its upper side, and is also permeable to oxygen transport into the liquid medium 2, accordingly. The liquid medium 2 is filled with a particular level $F_H$ in which the cells are allowed to be cultivated. In this embodiment, on the bottom of the vessel 1 two landing shaped members 5 are formed from an optically transparent material with the upper end face thereof is arranged in a particular distance H from the bottom surface of the vessel 1. Then, H is generally less than $F_H$.

On the end face of the left landing shamed member 5 a sensor membrane 3 is formed in order to exclusively measure oxygen concentration within the liquid medium 2.

On the end face of the right landing shaped member 5 an oxido-reductase membrane 4 is additionally formed on the oxygen sensitive sensor membrane 3.

Below the vessel 1 optical waveguides 6 including the light rays thereof (illustrated in dotted lines) aligned toward the sensor membranes 3 are arranged for one of the sensor membranes 3 and 3', respectively. By means of the optical waveguides 6 light can be directed upon the sensor membranes 3 and 3' for fluorescence excitation of a fluorescent dye contained in the sensor membranes 3 and 3'. In contrast, the fluorescent light of the sensor membranes 3 and 3' is allowed to be trapped by means of the optical waveguides 6.

Figure 2:
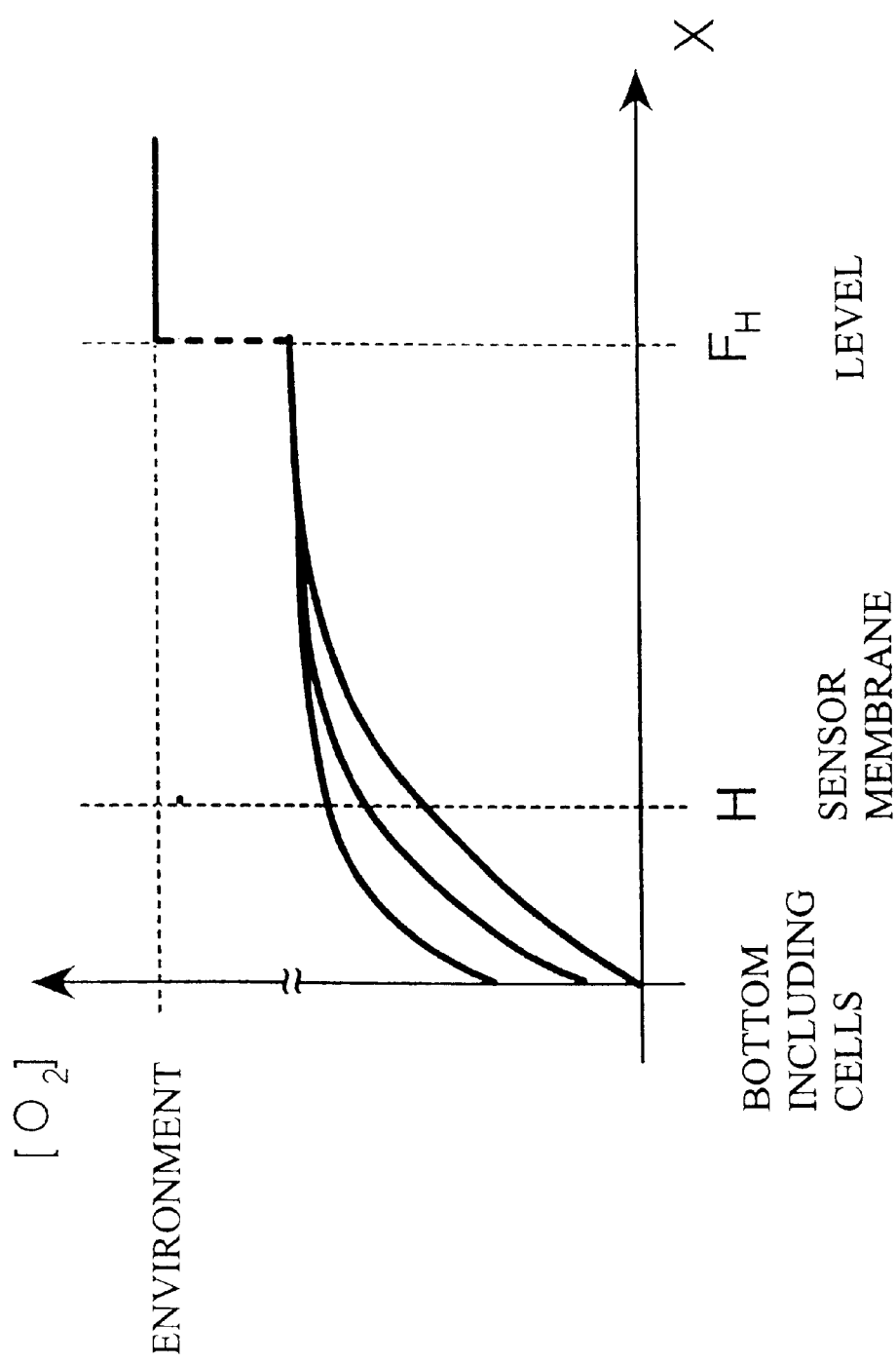
FIG. 2 shows a graph diagrammatically illustrating the oxygen concentration within the liquid medium from the culture cells containing bottom of the vessel up to the top surface of the medium contained in the vessel according to three different conditions.

In FIG. 2 is illustrated in a graph the oxygen concentration in the liquid medium 2 including culture cells which are located on the bottom, starting from the bottom of a vessel 1 up to the top surface of the liquid medium 2 according to three different conditions within the vessel 1. The bottom plot shows the course with a great oxygen consumption of the culture cells on the bottom, and the upper plot according to low oxygen.

It will be appreciated from the graph that considerably higher values of oxygen concentration in the liquid medium can be measured with a sensor membrane 3 located above the vessel bottom whereas the oxygen concentration on the bottom of a vessel 1 tends toward 0. This is caused by the oxygen consumption of the culture cells. Thus, it will be appreciated that a measurement on the bottom in close proximity to the cells is not meaningful. In addition, this graph reproduces the facts that with oxygen consumption of the culture cells the supply of oxygen into the liquid medium 2 can be detected with a sensor membrane located above the bottom across the surface thereof up to the cells. Thus, it will be appreciated that an oxygen measurement is only meaningful in the position between the culture cells and the places wherein the oxygen arrives into the liquid medium 2.

Figure 3:
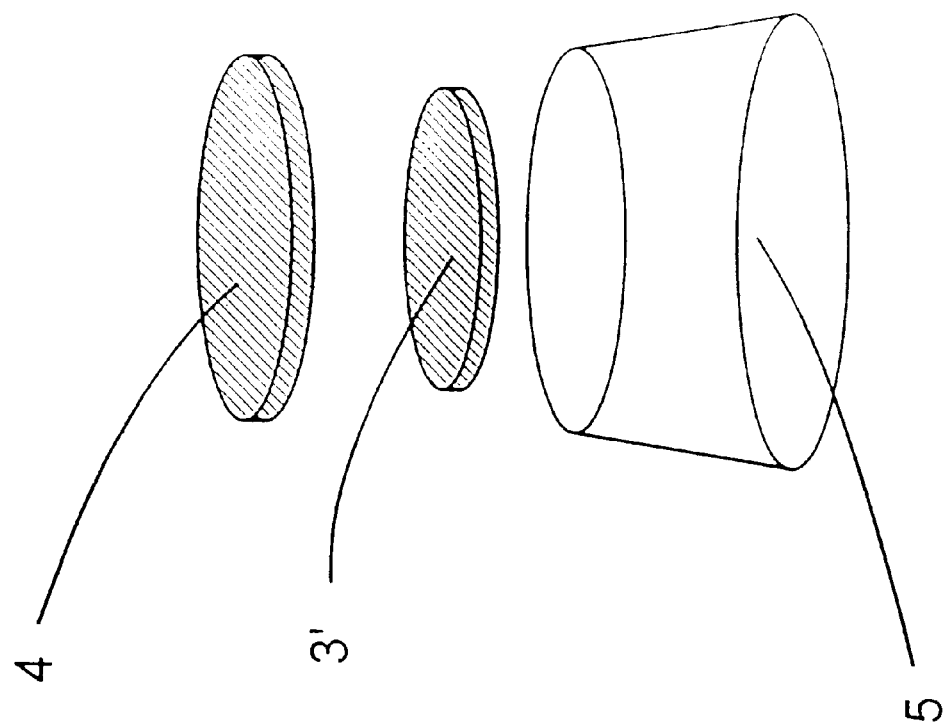
FIG. 3 shows diagrammatic illustrations of landing shaped members including oxygen sensitive membranes, and alternatively a supplementary oxido-reductase/membrane.
Figure 3:
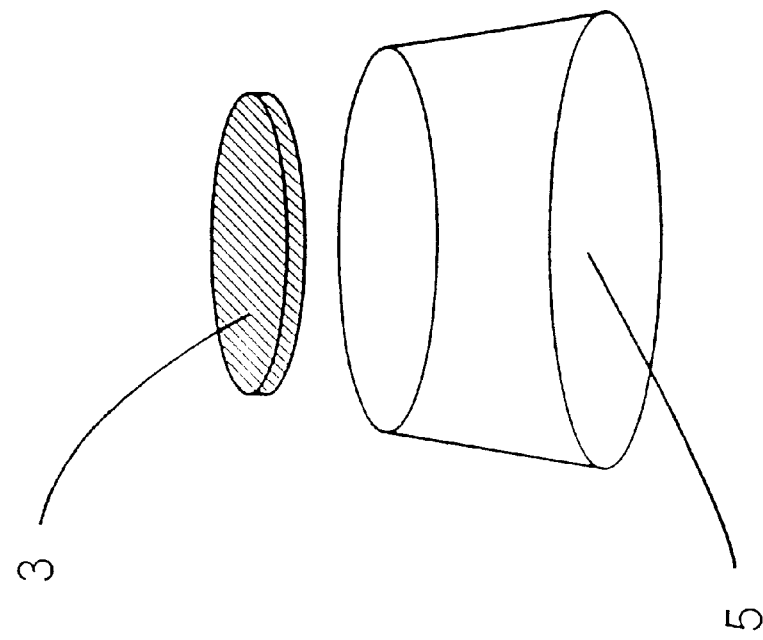

In FIG. 3 the improvement of landing shaped members 5 is diagrammatically shown wherein the left illustration shows a landing shaped member 5 which is exclusively provided with an oxygen sensitive membrane 3. Here, the landing shaped member 5 is formed in a truncated shape and is composed of a transparent material being at least approximately impermeable to oxygen wherein it is allowed to achieve that the measuring result will not be falsified by oxygen entering through the material.

Analogous to this is also formed the landing shaped member 5 illustrated in FIG. 3 on the right side wherein one supplementary oxido-reductase membrane 4 is merely provided above the oxygen sensitive membrane 3'.

Of course, the membranes 3, 3' and 4 are not formed, as illustrated here, above but immediately on the landing shaped members 5. Then, the oxido-reductase membrane 4 covers the oxygen sensitive membrane 3'.

Figure 4:
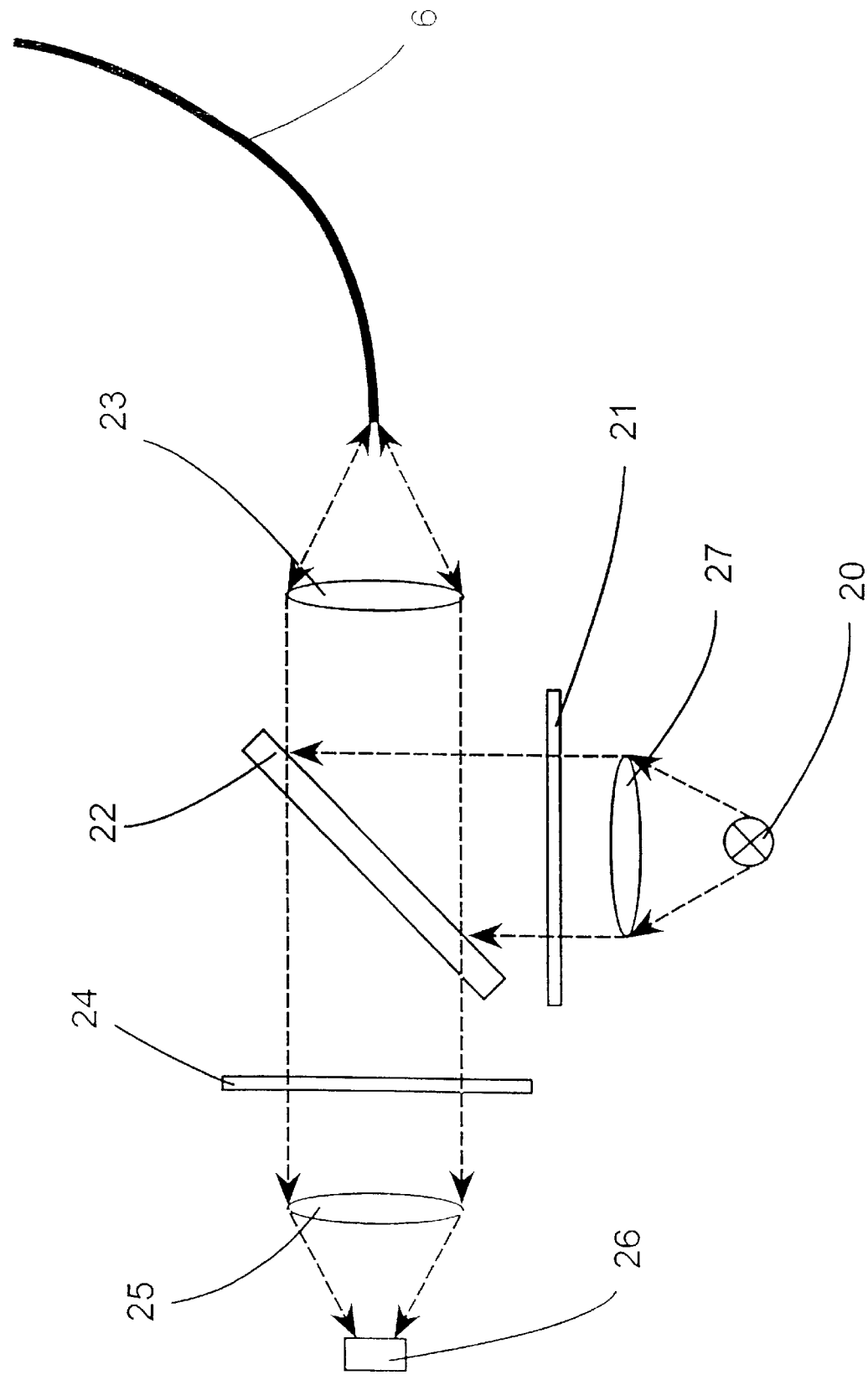
FIG. 4 shows diagrammatically a possibility of an optical measuring set-up for the generation and detection of fluorescent signals on a device according to FIG. 1.

In FIG. 4 an optical set-up is diagrammatically shown by means of which light of a light source 20 can be directed through an optical waveguide 6 upon an oxygen sensitive membrane 3 (not shown here) within a vessel 1 and a cavity 7, 7', respectively. The light source 20 preferably radiates approximately monochromatic light of a fluorescence exciting optical wavelength through an appropriate lens 27, as the case may be a filter 21 which essentially allows light having excitation light wavelength to pass through upon a dichroic beam splitter 22. Therefrom, light is coupled through a lens 23 into the optical waveguide 6. Of course, alternative known input gaps for optical waveguides 6 can be used as well. It is also possible to use a multi-spectral light source in combination with an appropriate filter wherein exclusively the filter provides the monochromatisation.

The fluorescent light then passes opposed to the excitation light through the optical waveguide 6 via the lens 6, the beam splitter 22, through a respective wavelength selected filter 24 which allows to pass fluorescent light only, as the case may be via another lens 25, upon an optical detector 26 by means of which the intensity of fluorescent light can be measured as a function of the respective oxygen concentration.

Figure 5:
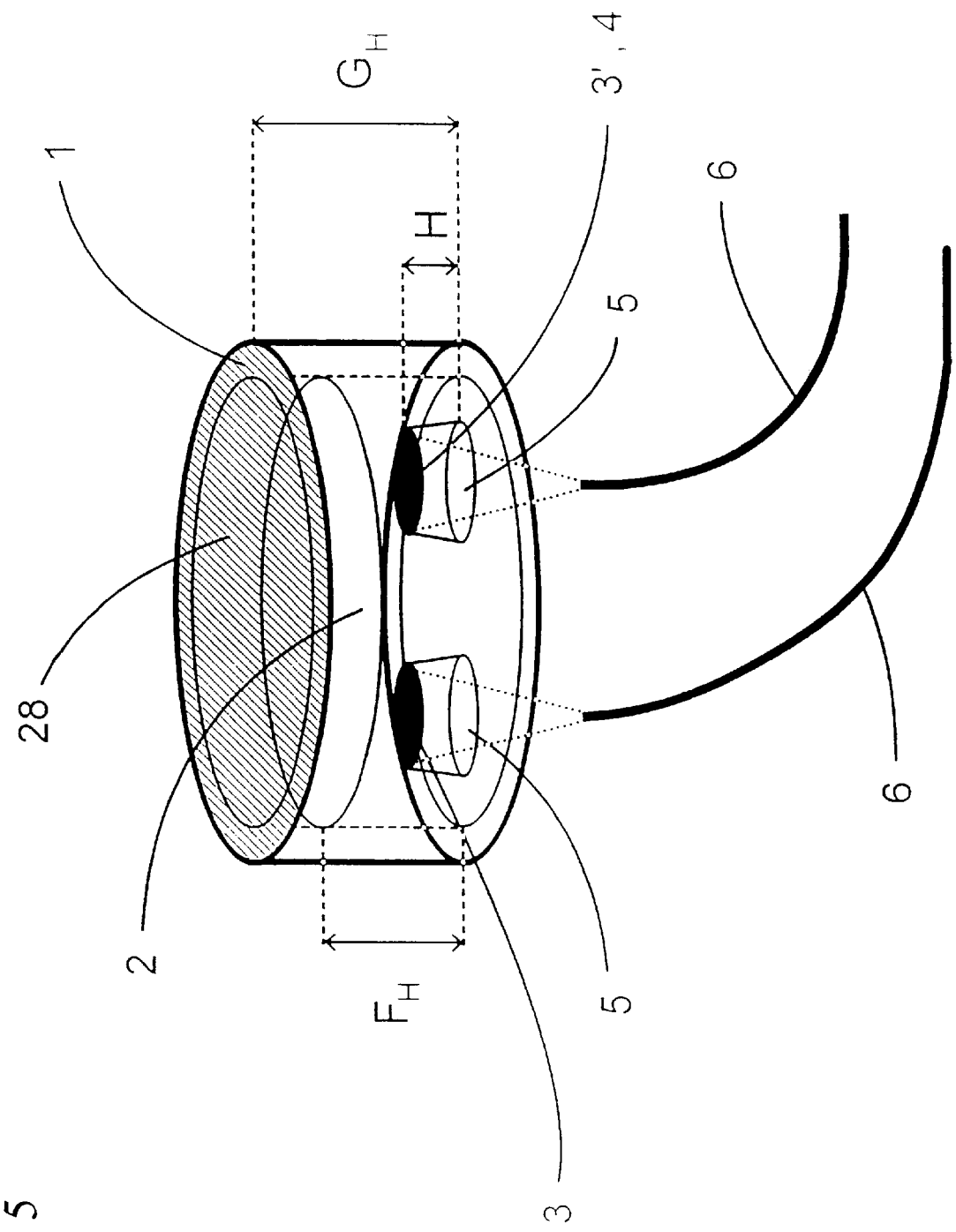
FIG. 5 shows a diagrammatic illustration of A another embodiment of a vessel comprising an oxygen permeable covering for monitoring metabolic activity of culture cells within liquid media.

The vessel 1 illustrated in FIG. 5 corresponds in the most significant points to the vessel already shown and described, respectively, in FIG. 1.

It is merely provided with a covering 28 which is admittedly permeable to oxygen, however, it prevents contaminations and consequently ensures the sterility. Moreover, drying out the vessel 1 can be prevented with such a covering 28.

In FIG. 5 it will be further recognized that the level $F_H$ is below the height $G_H$ of the vessel. $G_H$ Simultaneously reproduces the distance of the covering 28 of the vessel 1 from the bottom.

The oxygen gradient will be affected through the covering 28.

Figure 6:
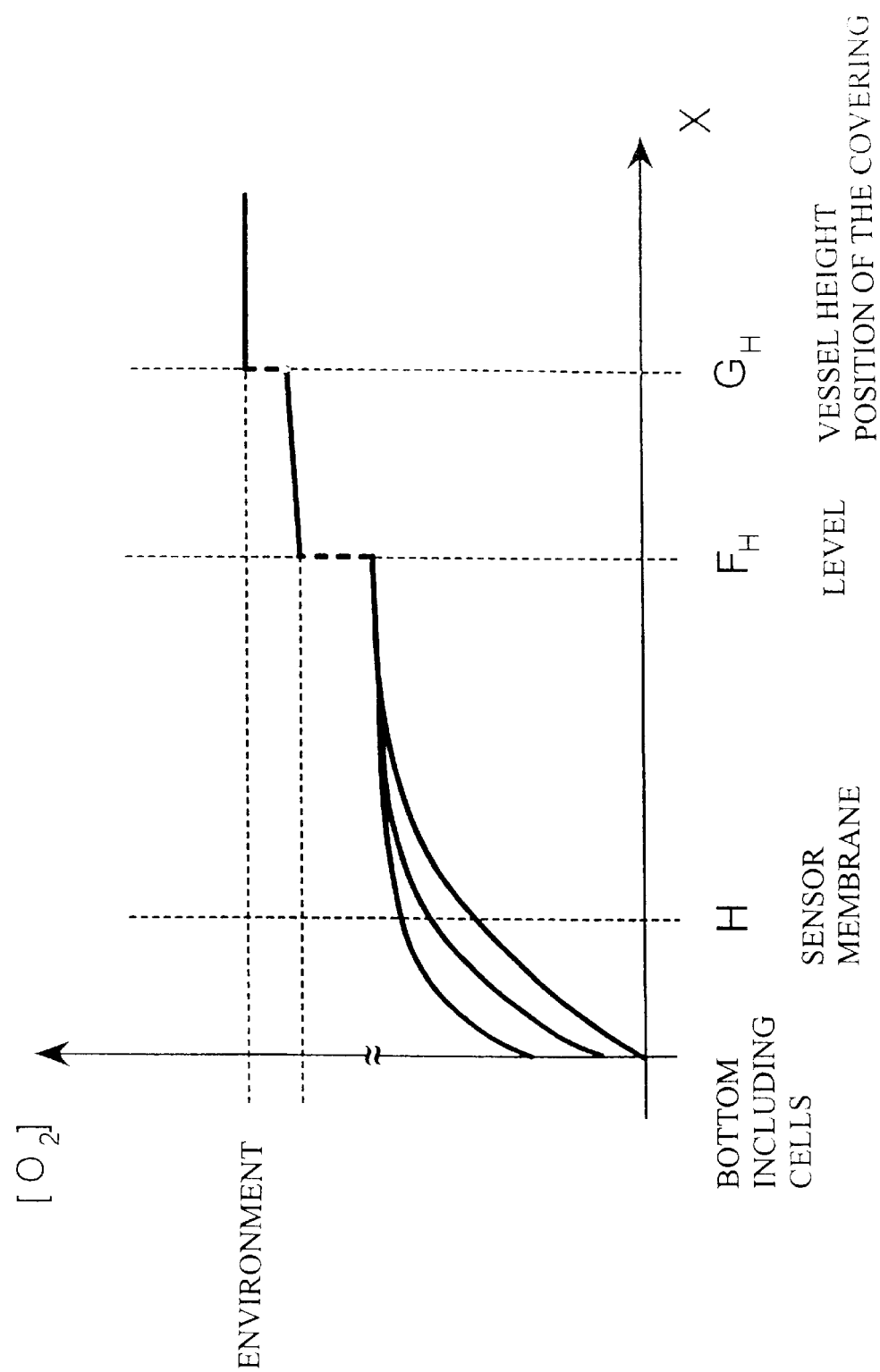
FIG. 6 shows a graph illustrating oxygen concentration in the liquid medium from the culture cells containing bottom of a vessel covered with an oxygen permeable membrane according to three different conditions up to the top surface of a liquid medium, and further up to the environment in which said vessel is contained.

These facts are reproduced in the graph according to FIG. 6, and it is intimated that oxygen concentration between the level $F_H$ and vessel height $G_H$ is subjected to a particular gradient of oxygen concentration as well which is elicited by the covering 28 during oxygen consumption caused by metabolic activity.

Figure 7:
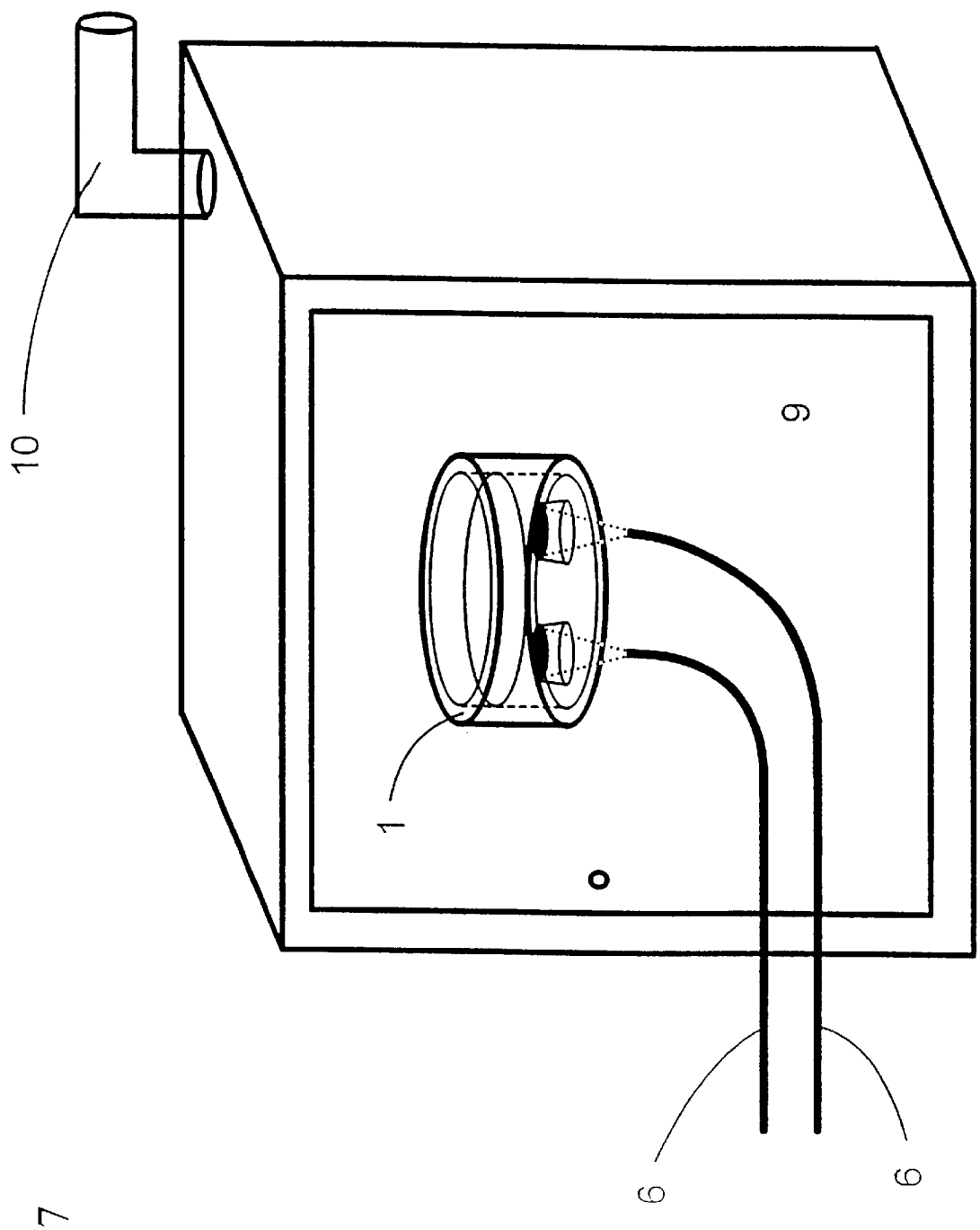
FIG. 7 shows a diagrammatic illustration of a vessel located within a breeding chamber according to FIG. 1.

With the embodiment shown in FIG. 7, a vessel 1 according to FIGS. 1 and 5, respectively, has been located within a typical breeding chamber 9 in which particularly optimum conditions for the cell cultivation can be met as is well known. On optimum conditions it is usually understood a temperature of approximately 37° C., a relative humidity of air of 100% at normal atmospheric pressure, and a partial oxygen pressure within the gas space corresponding to the ambient air. The optical waveguide 6 for the two sensor membranes 3 are allowed to be led out of the breeding chamber 9 such that a local separation between the measuring place and measured value detection can be achieved. Moreover, in this Figure is shown a gas supply 10 for the breeding chamber 9 through which atmospheric air having a respective constant content of oxygen can be supplied. Breeding chambers of the described type are employed for the cultivation of cells according to the standard.

Figure 8:
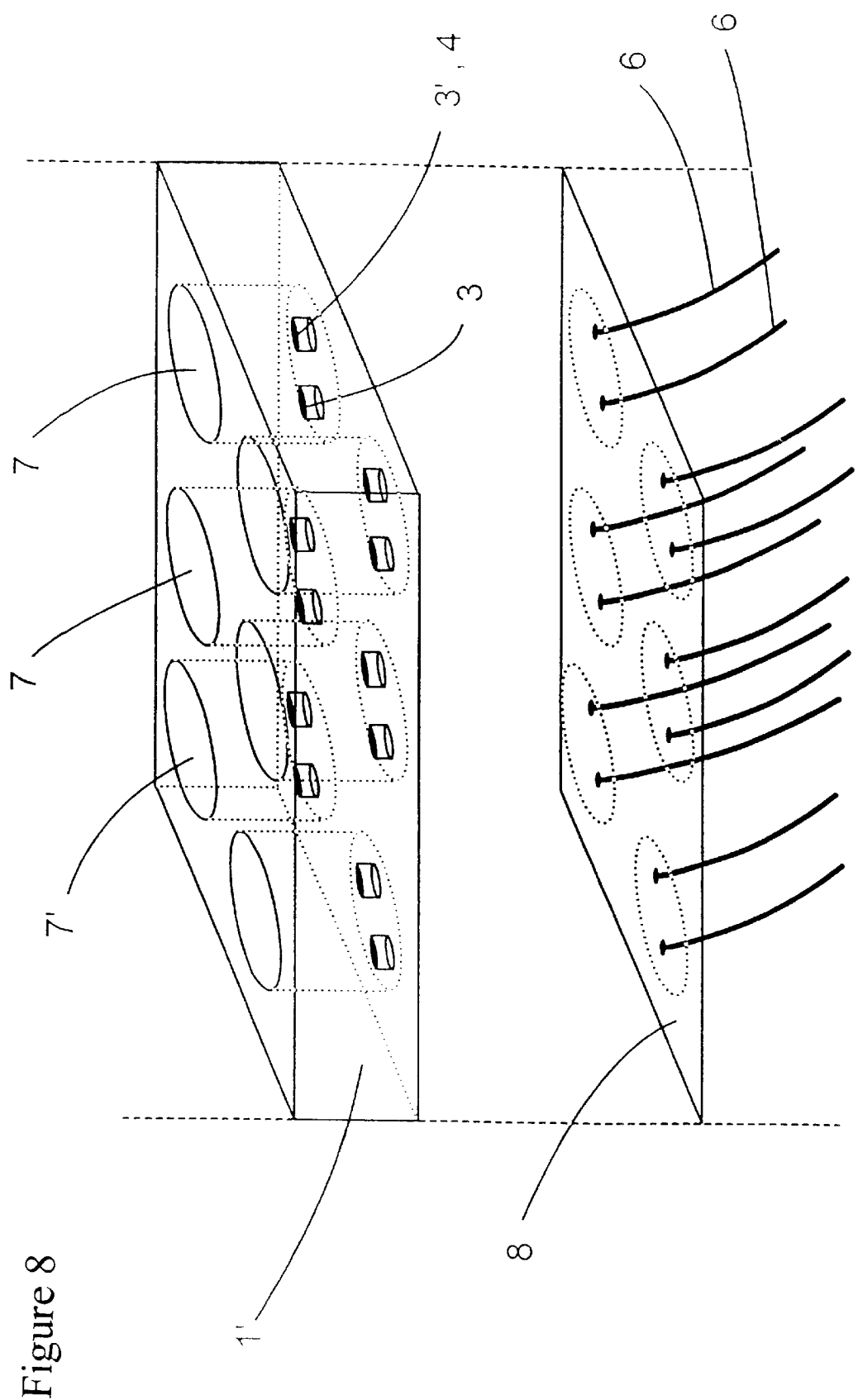
FIG. 8 shows a multi-purpose vessel in combination with a mechanism plate for optical waveguides which are connected to a device according to FIG. 4.

In FIG. 8 there is shown an embodiment for a vessel 1' to be used in accordance with the invention which is formed as a MicroWell™ Plate including a plurality of cavities 7, 7' which is very often used for the cultivation of cells. Two sensor membranes 3 and 3' are arranged and configured respectively again in the cavities 7, 7' wherein each sensor membrane 3' is further provided with an oxido-reductase membrane 4 in the analogous manner to the vessel 1, as it has been described and shown in FIG. 1.

Such a MicroWell™ Plate 1' can be located in a breeding chamber 9 again, and the cell cultures are allowed to be accordingly cultivated within the cavities 7. In the breeding chamber 9 a mechanism plate 8 can be arranged below the MicroWell™ Plate 1' by means of which the optical waveguides 6 can be fixed and positioned. Then, the optical waveguides 6 are supported to the mechanism plate 8 according to the arrangement of the sensor membranes 3 and 3' in the cavities 7 and 7' of the vessel 1'. The mechanism plate 8 is allowed then to be located within the breeding chamber 9 in such a distance to the MicroWell™ Plate 1', and here in particular to the bottom surface thereof such that the light rays from the optical waveguides 6 are able to detect the complete surface area of the respective sensor membranes 3 and 3' associated therewith. Using the mechanism plate 8 permits an operation being undisturbed for the cell cultivation. In the breeding chamber the cells will not be subjected to any further treatment. For such purposes the MicroWell™ Plate 1' is removed from the breeding chamber, and thus from the support 8. Outside the breeding chamber, the treatment of the cell cultures can be taken place then in the common sense, without any resrictions such as e.g. a change of the liquid medium 2 or monitoring the cells with a microscope.

At least one cavity 7' of such a MicroWell™ Plate 1' can be used for the reference measurement already explained by filling this cavity 7' without cells only with liquid medium 2.

Figure 9:
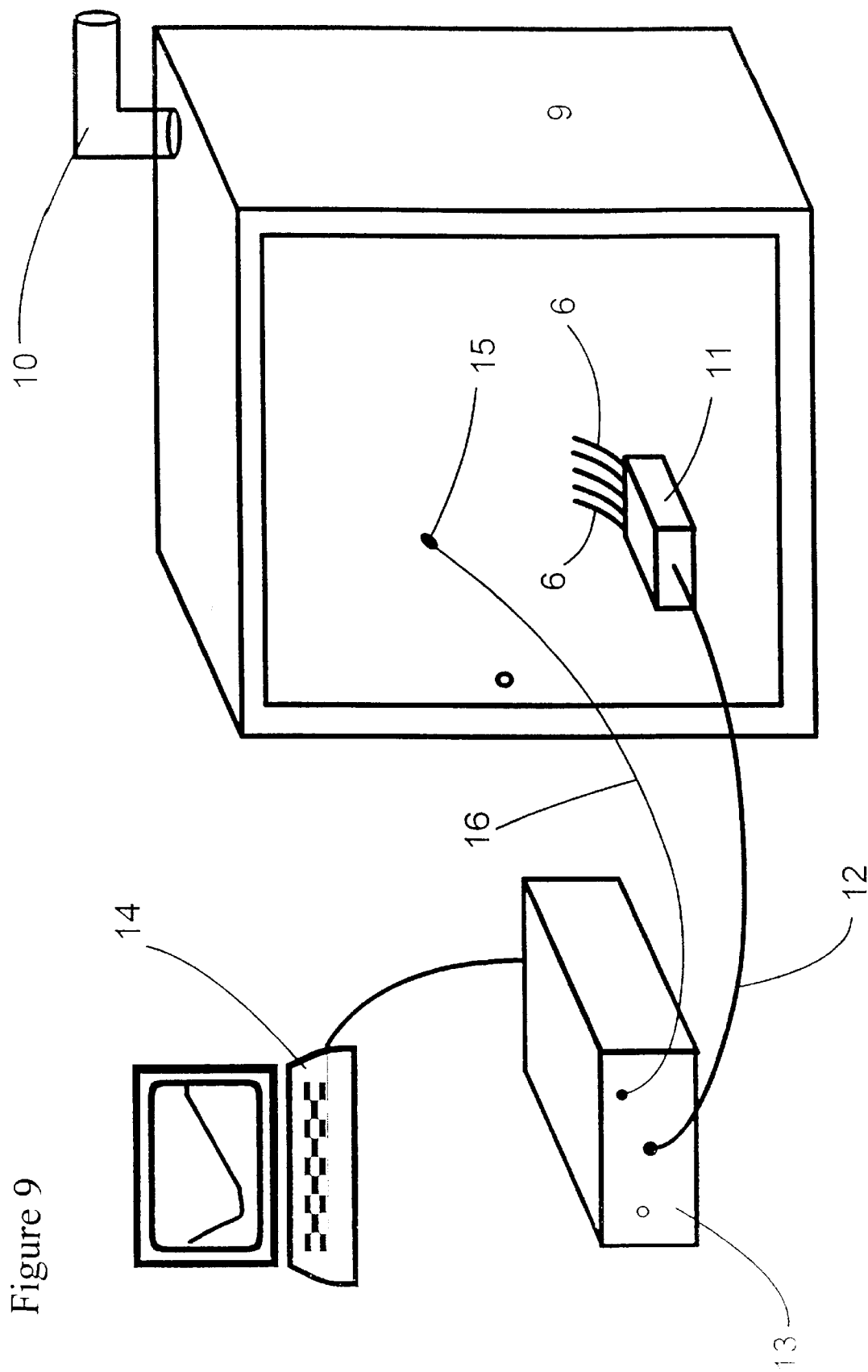
FIG. 9 shows a diagrammatic illustration of a multiplex detection of a plurality of samples.

In the illustration according to FIG. 9 an optical multiplex operation is diagrammatically shown by means of which a spatial resolution type measurement in addition to the time resolution type measurement as well of several samples is enabled which are contained in different vessels 1 and cavities 7 and 7', respectively. Thus, FIG. 9 shows a complex set-up for implementing the method according to the invention.

An array of the light source 20, detector 26, lenses 23, 25, 27, filters 21, 24 and beam splitters 22 as illustrated in FIG. 4 is located within a transmitting and measuring unit 13 outside the breeding chamber 9. The excitation light is guided from this transmitting and measuring unit 13 via a single optical waveguide 12 into an optical multiplexer 11 wherein further optical waveguides 6 are connected. The optical multiplexer 11 sequentially directs the fluorescent excitation light through the single optical waveguides 6 for the fluorescent excitation toward the different sensor membranes 3 and 3'.

The fluorescent light of the different sensor membranes 3 and 3' again arrives via the optical waveguides 6 to the optical multiplexer 11, and is sequentially directed therefrom upon an optical detector which is included in the unit 13 corresponding to the respective measurement locations, that is the respective sensor membranes 3 and 3' according to the respective sample vessel 7 and 7', respectively, via the optical waveguide 12. The signals thus detected can be employed in a correspondingly spatial and time type resolution manner for the determination of the respective oxygen concentration and the oxido-reductase substrate concentration.

From the unit 13 the detected measured values pass to a benchmarking and control unit 14 which is a personal computer here by means of which the benchmarking of the detected measuring signals, and then in particular the value comparison indicated in the general part of the description can be carried out by measurement in the reference vessel 7'. With the benchmarking and control unit 14 the transmitting and measuring unit 13 and optical multiplexer 11 as well can be controlled.

Moreover, inside the breeding chamber 9 are arranged sensors 15 for detecting the temperature, the relative humidity of air, the gas pressure and chemical composition as may be the case, including the respective partial pressure of involved gases of the gaseous atmosphere. The measured values detected by the sensors 15 are directed again via a separate line 16 into the transmitting and control unit 13, and therefrom into the benchmarking and control unit 14 such that the value comparison indicated in the general part of the description thus can be carried out. But there is the possibility either to direct the line 16 immediately from the sensors 15 to the benchmarking and control unit 14. According to the sensor data the saturation concentration of oxygen in the reference vessel 7' can be calculated as shown in the general part of the description, and thus the value comparison is allowed to occur.

Figure 10:
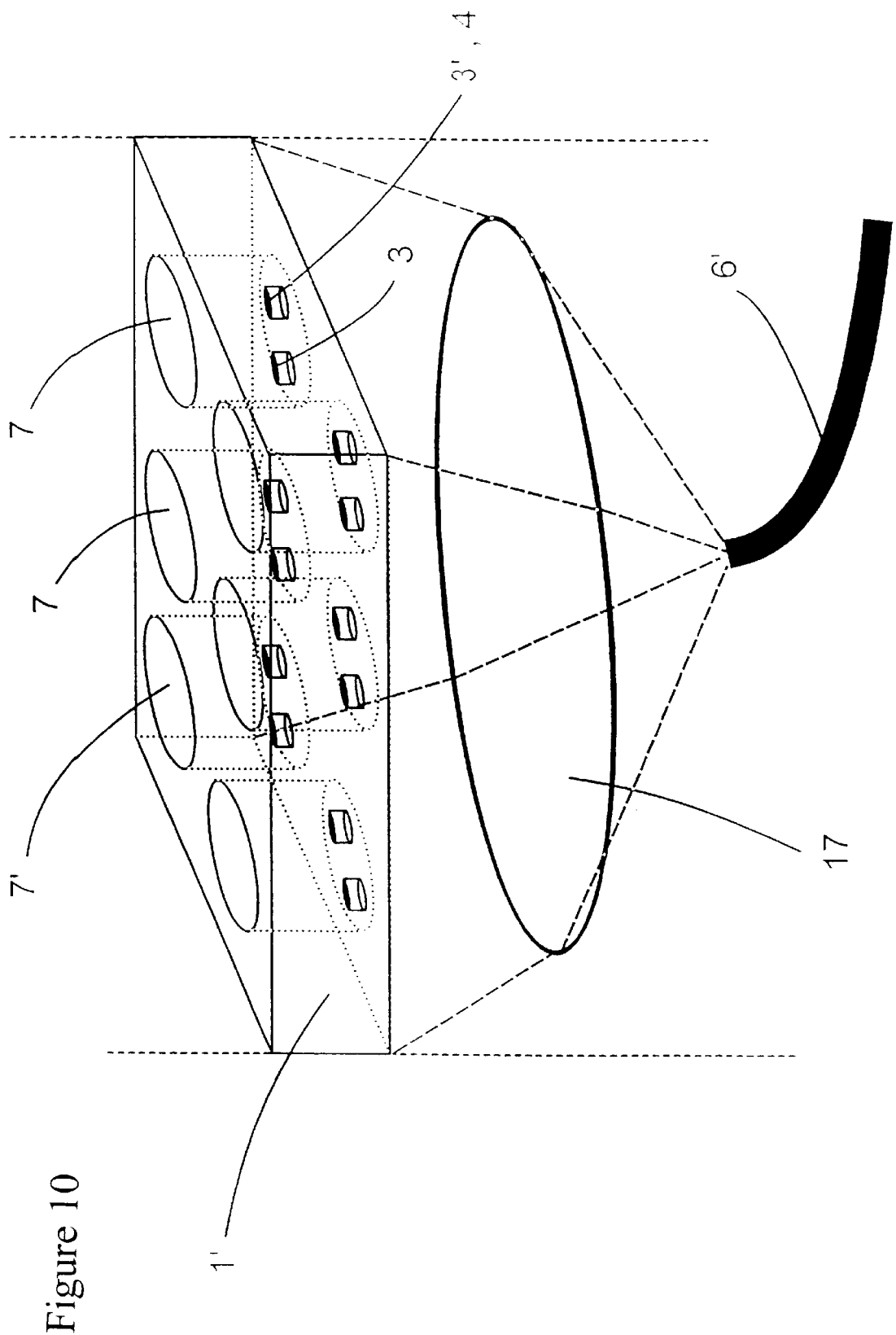
FIG. 10 shows an embodiment of a device according to the invention wherein a MicroWell™ Plate is monitored by means of an imaging optics, e.g. an endoscopy array.

In FIG. 10 an embodiment for simultaneously monitoring more samples is reproduced which are contained in a plurality of cavities 7 and 7' of a MicroWell™ Plate 1'. Then, below the MicroWell™ Plate 1' a focussing lens 17 is mounted by means of which at least that part of the MicroWell™ Plate 1' on which the membranes 3 and 3' are arranged, on the one hand, is radiated with the excitation light, and, on the other hand, the respective fluorescent signal can be coupled as images into a light guiding system used as an optical waveguide bundle 6', is allowed to be imaged and passed on.

Figure 11:
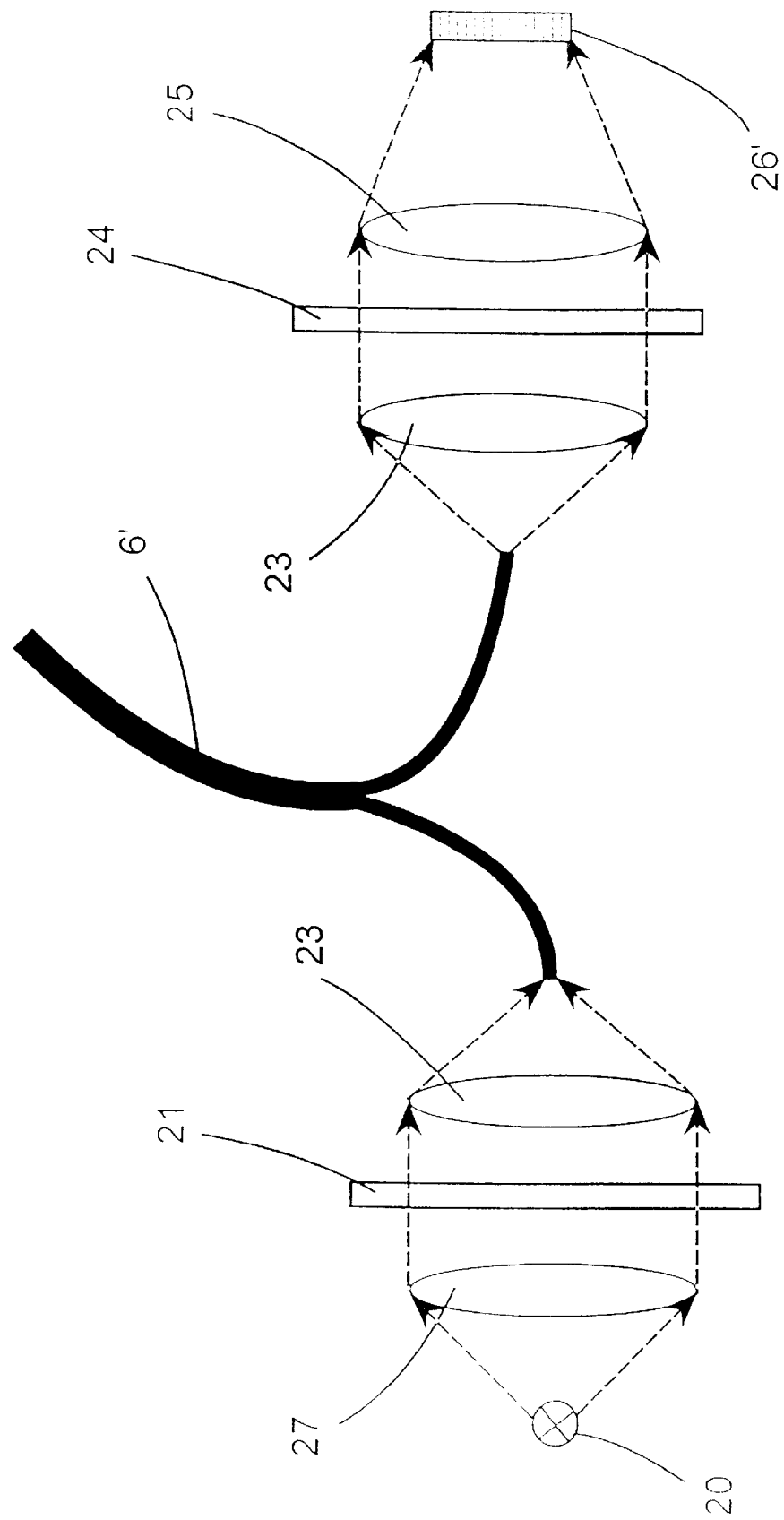
FIG. 11 shows the optical part of a device according to FIG. 10 for the generation and detection of fluorescent signals.

The excitation and detection by fluorescent signals on the membranes 3 and 3' within the cavities 7 and 7' is allowed then to occur by way of example as shown in FIG. 11. Therewith, light of a light source 20 is coupled again via a lens 27, a filter 21 and a couple optics 23 at least into one part of the optical waveguide bundle 6', and is directed upon the membranes 3 and 3' which are located on landing shaped members within the cavities 7 and 7', as already described a number of times, wherein only light from the light source 20 having a fluorescence exciting wavelength is used by means of the filter 21.

The fluorescent light of the different membranes 3 and 3' again arrives, as diagrammatically shown here, from the other part of the optical waveguide bundle 6' via the two lenses 23, 25 and an accordingly appropriate filter 24 upon an optical detector 26' which here is a camera appropriate for a spatial resolution type measurement. Therewith, the fluorescent signal of the individual membranes 3 and 3' of the cavities 7 and 7' can be detected again in a spatial resolution manner.

Figure 12:
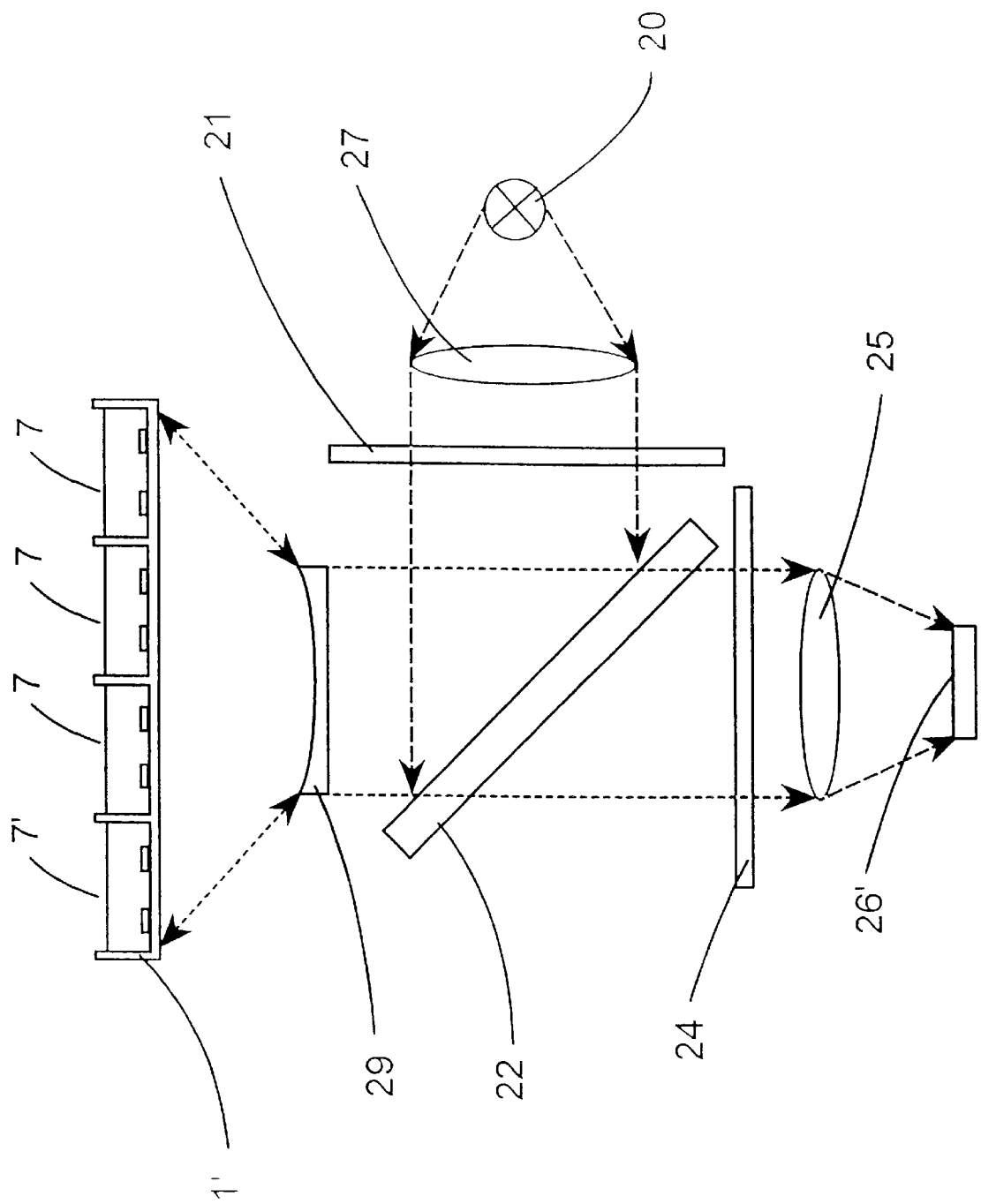
FIG. 12 shows an embodiment of an optical system for the generation and detection of fluorescent signals on a MicroWell™ plate for simultaneously monitoring a plurality of cell cultures.

In FIG. 12 is shown another embodiment of an optical set-up for simultaneously monitoring different samples which are located in a plurality of cavities 7 and 7' of a MicroWell™ Plate 1'.

Then, light of a light source 20 is directed again via a filter 21 for fluorescent excitation upon the different oxygen sensitive membranes 3 and 3' through the bottom of the vessel 1' which is formed in a transparent manner at least in the area of the landing shaped members 5. For beam forming and beam guiding again the different lenses 27 and 29 and a dichroic beam splitter 22 as well are used.

The fluorescent light of the different membranes 3 and 3' passes via the lens 29 through the diochroic beam splitter 22, and an appropriate filter 24 as may be the case, upon an optical detector 26' which again can be a camera 26' here appropriate for a spatial resolution type measurement. Imaging the fluorescent light can occur by means of a supplementary lens 25 upon the camera 26'.

What is claimed is:

1. A method for monitoring metabolic activity of cells cultivated in liquid media, wherein said cells are received in vessels which are partially permeable to the mass transport of oxygen into the liquid medium, wherein the oxygen concentration is measured optically with the aid of sensor membranes in said liquid medium positioned between the cultivated cells and the part of the vessel which is dominantly permeable to oxygen transport into said liquid medium; and said oxygen concentration measured in said liquid medium is compared with an oxygen concentration value measured in a reference vessel containing only liquid medium without cells, and/or an oxygen concentration value calculated by means of measured values of other parameters.

2. A method according to claim 1, wherein the temperature of said liquid medium is determined in said vessel and/or said reference vessel, and the relative humidity and pressure outside said vessels are measured, and a corresponding oxygen concentration is calculated from the respective measured values.

3. A method according to claim 2, wherein the temperature of said liquid medium is directly measured in said vessels.

4. A method according to claim 2, wherein the temperature in said vessels is indirectly measured through the ambient temperature.

5. A method according to claim 1, wherein in the event of a variable chemical composition of the ambient atmosphere of said vessel and reference vessel, the oxygen concentrations are determined with respect of the composition of the ambient atmospheres.

6. A method according to claim 1, wherein a second oxygen sensor membrane coated with an appropriate oxido-reductase is positioned between the cultivated cells and the part of said vessel which is dominantly permeable to the oxygen transport in said liquid medium.

7. A method according to claim 6, wherein said oxygen concentrations measured with said first oxygen sensor membrane and said second oxygen sensor membrane in said vessel are correlated with each other to determine the oxido-reductase substrate concentration.

8. A method according to claim 1, wherein the metabolic activity of the cultivated cells is monitored with the aid of a time resolution type measurement of the oxygen concentration including the oxygen consumption of said culture cells determined therefrom.

9. A method according to claim 1, wherein the fluorescent intensity or fluorescence decay time of a fluorescent substance contained in said sensor membranes will be measured, wherein the fluorescent substance has a fluorescence extinction relating to the oxygen concentration.

10. A method according to claim 1, wherein the oxygen concentration in the liquid media of a plurality of vessels and reference vessels is measured in a spatially resolved manner.

11. A device for monitoring metabolic activity of culture cells in liquid media comprising a vessel which at least is partially composed of an optically transparent material and which is partially permeable to the oxygen transport, and at least one sensor membrane for the optical measurement of the oxygen concentration is located in said liquid medium, wherein the at least one sensor membrane is located inside said vessel between said cultivated cells and the part of said vessel which is dominantly permeable to the oxygen transport in said liquid medium.

12. A device according to claim 11, wherein said sensor membranes are deposited on the inner wall and/or on at least partially transparent landing shaped members which are located on the vessel bottom.

13. A device according to claim 11, wherein the vessel comprises an aperture that is covered with an oxygen permeable membrane.

14. A device according to claim 11, wherein a plurality of vessels are configured in the form of a multi-well plate.

15. A device according to claim 11, further comprising an optical waveguide and a light source, wherein the light source directs light of an approximately monochromatic light source or light having a wavelength exciting fluorescence that has been passed through an optical filter onto said sensor membrane via the optical waveguide.

16. A device according to claim 15, further comprising an optical detector, wherein the light is directed through an optical filter onto the optical detector via said optical waveguide or a supplementary optical waveguide.

17. A system comprising a device according to claim 15, further comprising a multiplexer, wherein said optical waveguide is connected to the multiplexer.

18. A device according to claim 15, wherein said optical waveguide is positioned by means of a mechanism plate with respect to said sensor membranes in said vessel.

19. A device according to claim 15, wherein light from the light source is directed upon said sensor membrane through an imaging optical waveguide, similar light guiding systems or optical elements.

20. A device according to claim 11, wherein said sensor membrane is viewed by means of an imaging optical waveguide, similar light guiding systems or optical elements, and the images thereof are directed upon a linear or planiform array of light sensitive detectors.

21. A device according to claim 11, further comprising an incubator, wherein said vessel is located in the incubator.

22. A device according to claim 11, further comprising one or more sensors for determining the temperature, the relative humidity of air, and the pressure of the gaseous atmosphere, wherein the sensors are present in the immediate vicinity of the vessel.

* * * * *